United States Patent [19]

Bonaldo

[11] Patent Number: 5,306,243
[45] Date of Patent: * Apr. 26, 1994

[54] MEDICAL VALVE

[75] Inventor: Jean M. Bonaldo, Upland, Calif.

[73] Assignee: Care Medical Devices, Inc., Ontario, Calif.

[*] Notice: The portion of the term of this patent subsequent to Dec. 28, 2010 has been disclaimed.

[21] Appl. No.: 90,735

[22] Filed: Jul. 12, 1993

Related U.S. Application Data

[63] Continuation-in-part of Ser. No. 849,520, Mar. 11, 1992, Pat. No. 5,273,533.

[51] Int. Cl.⁵ .............................................. A61M 37/00
[52] U.S. Cl. .......................................... 604/86; 604/83; 604/167; 604/244; 604/283
[58] Field of Search .................. 604/83, 86, 87, 88, 604/167, 244, 246, 256, 283, 905

[56] References Cited

U.S. PATENT DOCUMENTS

| | | | |
|---|---|---|---|
| 4,080,965 | 3/1978 | Phillips . | |
| 4,121,585 | 10/1978 | Becker, Jr. | 604/86 |
| 4,511,359 | 4/1985 | Vaillancourt . | |
| 4,512,766 | 4/1985 | Vaillancourt | 604/256 |
| 4,617,012 | 10/1986 | Vaillancourt . | |
| 4,950,260 | 8/1990 | Bonaldo . | |
| 5,065,783 | 11/1991 | Ogle, II . | |
| 5,088,984 | 2/1992 | Fields | 604/905 |
| 5,122,123 | 6/1992 | Vaillancourt . | |
| 5,154,703 | 10/1992 | Bonaldo | 604/905 |

Primary Examiner—C. Fred Rosenbaum
Assistant Examiner—N. Kent Gring
Attorney, Agent, or Firm—Robert R. Thornton

[57] ABSTRACT

A valve for medical use has a cannula mounted on a hub and fixed in a fluid conduit so that the cannula points upstream. An elastomeric valve element is mounted on the hub within the conduit so as to enclose the cannula. The valve element has a first solid portion of circular cross-section disposed upstream of the cannula point which closes the conduit, a second hollow frustoconical portion within which the cannula point is disposed, and a third hollow cylindrical portion surrounding the cannula downstream from its point and fixed to the hub. The second portion has a frustoconical interior passageway. In use, the valve element is compressed by application of a medical appliance to the valve element first portion to cause the cannula point to pierce the first portion to provide a path for fluid flow through the conduit.

18 Claims, 4 Drawing Sheets

"5,306,243"

MEDICAL VALVE

CROSS-REFERENCE TO RELATED APPLICATION

This application is a continuation in part of my copending application Ser. No. 07/849,520, filed Mar. 11, 1992, now U.S. Pat. No. 5,273,533.

BACKGROUND OF THE INVENTION

1. Field of the Invention

The present invention relates to a valve for medical use in a fluid conduit to prevent the back-flow of blood or other fluid upstream of the valve and, while it is particularly adapted for use in multiple inlet connectors such as Y-site ports, may be used in simple inlet connectors as well.

2. Description of the Prior Art

U.S. Pat. No. 4,512,766, issued Apr. 23, 1985 to Vincent L. Vailancourt, discloses a valve mechanism for catheter use to avoid fluid backflow, including an elastomeric self-sealing valve element which may be pierced by an external needle used to insert a catheter. In an alternate embodiment, the valve element is pre-slit and is opened by an internal insert tube when the valve element is compressed by an external adaptor fitted, for example, on a medication administration set.

SUMMARY OF THE INVENTION

According to the present invention, a valve for medical usage within a rigid fluid conduit has, as a first component, a hub fixed within the conduit so as to hold a cannula so that the cannula lumen opens onto a point which points away from the hub and, as a second component, an elongated flexible valve element having a first solid portion of circular cross-section which extends from a base which forms an internal seal of the conduit to a top, a second hollow portion of circular cross-section which is at least in part frustoconical with its base formed on the first element top so as to continue the frustoconical taper, and a third portion which is cylindrical and connected to the second portion so as to extend away from said second portion and terminate in a valve outlet, the first, second, and third portions being axially aligned with one another, and in which the third portion has a longitudinal passage extending therethrough so as to be in direct communication with and axially aligned with the interior of the second portion, the second portion interior being generally frustoconical so as to open outwardly between the third portion and the first portion, and within which a rigid supplementary frustoconical sleeve is disposed so as also to open outwardly between the third portion and the first portion, and in which the third portion is attached to the hub so that the valve first and second portions normally enclose the cannula and the valve third portion forms an internal seal of the conduit at the conduit inlet by extending slightly beyond the conduit inlet.

BRIEF DESCRIPTION OF THE DRAWING

The medical valve of the invention is illustrated in the accompanying drawing, in which like numerals indicate like parts, and in which.

DETAILED DESCRIPTION OF THE PREFERRED EMBODIMENTS

Figure 1:
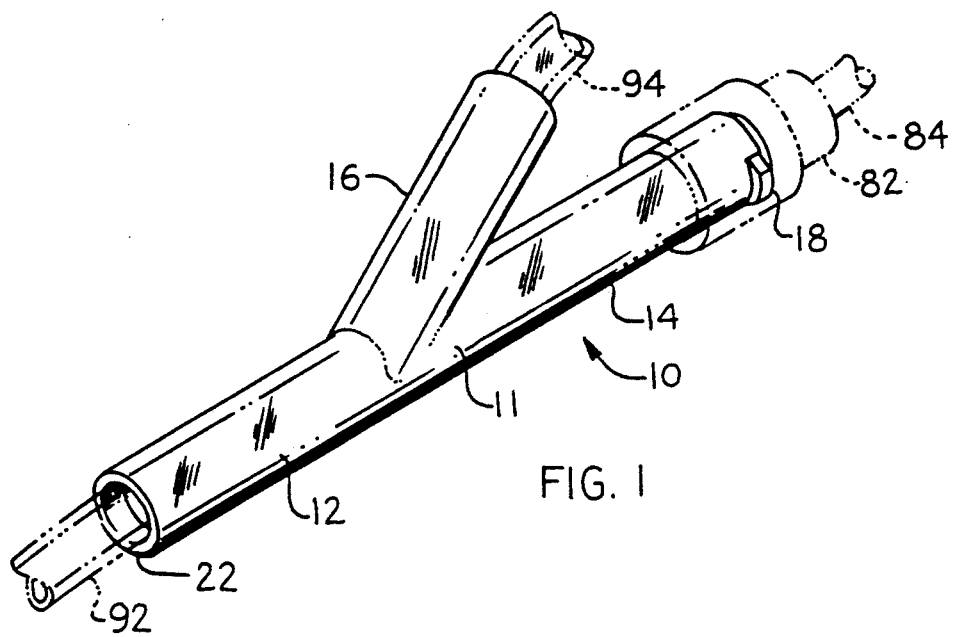
FIG. 1 is a isometric view of a Y-site port-type connector for use with a medical valve according to the present invention.

Referring now to FIG. 1, there is shown, in perspective, a Y-site port type connector 10 for use with a medical valve according to the present invention. The port 10 has a body 11 from which extend an outlet arm 12, a first inlet arm 14, and a second inlet arm 16. Luer-type lock lugs 18 (only one of which is shown in FIG. 1) extend outwardly from the first arm 14 for use in attaching other medical devices to the arm 14. If desired, the lugs 18 may be omitted, or similar lugs may be added to the other arms 12, 16. As is seen in FIG. 1, the first arm 14 and second arm 16 intersect one another at an acute angle and the arm 14 is generally longitudinally aligned with the outlet arm 12. Any other configuration may be equally used with respect to the present invention, or the arm 16 omitted if multiple inlets are not desired.

Figure 2:
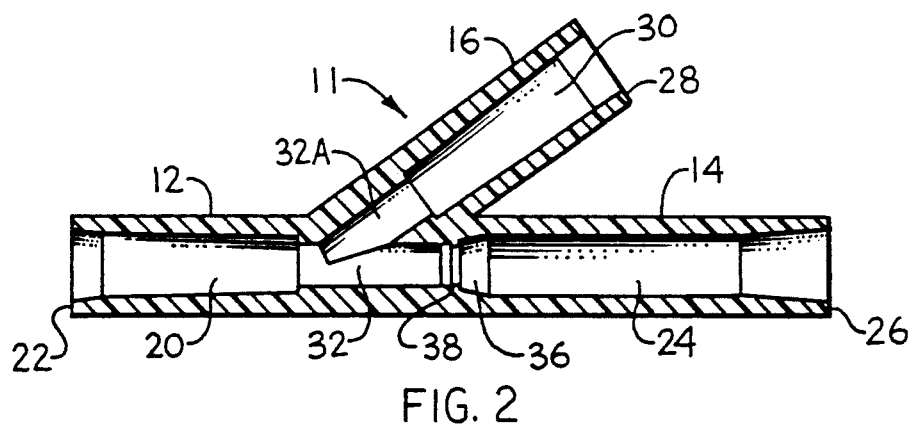
FIG. 2 is a cross-sectional view of a port body for the connector as shown in FIG. 1.

Referring now to FIG. 2, there is shown, in section, the body portion 11 of the port 10 shown in FIG. 1. As is seen in FIG. 2, the outlet arm 12 is hollow and generally cylindrical in cross-section with a passage 20 extending from an outlet 22 formed on the outlet arm 12 inwardly toward the inlet arms 14, 16. The inlet arm 14 has a passage 24 which extends from a first arm inlet 26 toward the outlet arm passage 20. The second inlet arm 16 has a second arm inlet 28, from which a second inlet passage 30 extends toward the outlet passage 20. The outlet passage 20 and inlet passages 24, 30 meet in a central chamber 32. For the particular embodiment shown in FIG. 2, the central chamber 32 is axially aligned with the first inlet arm passage 24 and the outlet arm passage 20. The second inlet arm passage 30 communicates with the central chamber 32 through a chamber extension 32A. Obviously, it is not necessary that the outlet arm 12 be aligned with either of the inlet passages 24, 30, so long as the three passages 20, 24 and 30 communicate directly with one another, such as by the central chamber 32 and chamber extension 32A shown in FIG. 2.

Figure 3:
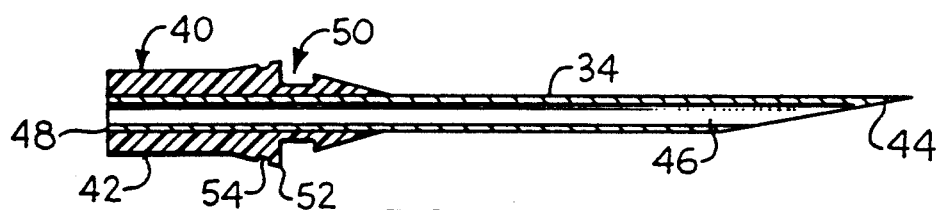
FIG. 3 is a cross-sectional view of a needle and hub assembly for use in a medical valve according to the present invention.

FIG. 3 is a cross-sectional view of a cannula 34 for use in the port body 11 by being fixed in the first outlet arm passage 24. As will be seen in FIG. 2, the first inlet arm passage 24 communicates with the central chamber 32 through a connecting passage 36 which tapers inwardly from the first inlet arm passage 24 to the central chamber 32. An annular lip 38 is formed in the connecting passage 36. The cannula 34 is mounted on a hub 40 which has a body portion 42 formed on the cannula opposite the cannula's point 44. The cannula has a lumen 46 which extends through the cannula from the point 44 to a cannula end 48 opposite the point 44. The hub body portion 42 has a value element locking recess 50 formed adjacent one end thereof. The other end of the hub body portion 42 is mounted about the cannula end 48 and tapers radially outwardly therefrom to a shoulder 52, on which an peripheral ring 54 is formed. As will be seen with respect to FIG. 5, the peripheral ring 54 engages the annular lip 38 on the body 11 so as to lock the hub end 40 and so the cannula 34 within the first inlet arm passage 24.

Figure 4:
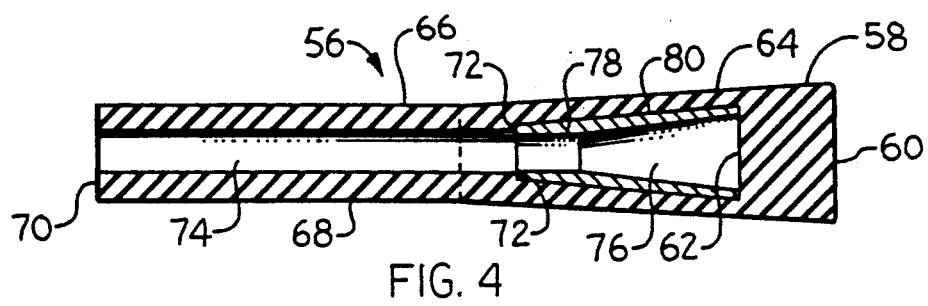
FIG. 4 is a cross-sectional view of a valve element for use in the first embodiment of the medical valve of the present invention.

Referring now to FIG. 4, there is shown an elongated valve element 56 for use in the present invention. The valve element 56 may typically be constructed of an elastomeric material such as latex commonly used in medical applications. The valve element 56 has a first portion 58 which is generally frustoconical in shape so as to taper from a base 60 forming a first end of the valve element 56 to a top 62. The valve element 56 has a second portion 64 which is generally frustoconical in exterior configuration over the majority of its length and tapers from the top 62, which forms the base of the second portion 64, to a second portion top 66, shown in dotted lines in FIG. 4. The valve element 56 has a third portion 68 which is generally cylindrical in configuration and extends from the second portion top 66 to a second end 70 of the valve element 56 which, in operation, engages the valve element locking recess 50 on the hub body portion 42 (see FIGS. 5 and 6).

As will be seen in FIG. 4, the third portion 68 has a cylindrical passageway 74 extending therethrough from the valve element second end 70 to the second portion top 66. The second portion 64 has an interior passageway 76 which is generally frustoconical in shape over most of its length so as to taper outwardly between a shoulder 72 formed adjacent the second portion top 66 and the first portion top 62. In the particular embodiment shown, the cylindrical passage from the third portion passage 74 extends onward into the interior of the second portion 64 a short distance before opening onto the shoulder 72 in the second portion interior passageway 76. The valve portions 58, 64, 68 are axially aligned with one another and provide a central passageway consisting of the passageways 74 and 76, within which the hub 40 and cannula 34 are disposed, as shown in FIG. 5.

Seated within the cylindrical passageway 76 against the shoulder 72 is a frustoconical sleeve 78 which preferably is made of stainless steel. The frustoconical sleeve 78 has an exterior surface which conforms with the interior surface 80 of the passageway 76. Thus, as will be explained hereinafter, the frustoconical sleeve 78 serves as a supplemental sleeve to provide additional strength and an impervious inner surface for the interior surface 80 of the passageway 76.

Figure 5:
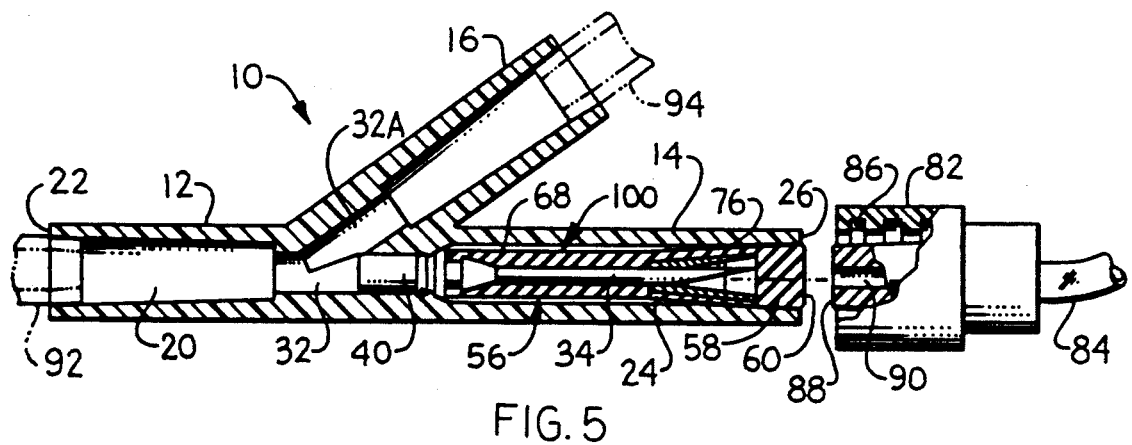
FIG. 5 is a cross-sectional view of the components illustrated in FIGS. 3, and 4 assembled in the body of FIG. 2 and ready to receive a medical device having a female Luer fitting.

Referring now to FIG. 5, there is shown a side elevational view of the port 10 adapted for use with respect to the attachment to the inlet arm 12 of a Luer-type fitting 82 from which a surgical tube 84 of conventional construction extends so as to selectively apply fluid to the fitting 82. The fitting 82 has a female Luer thread 86 which engages the lug 18 on the port 10 shown in FIG. 1.

The Luer-type fitting 82 has a nose 88 of conventional construction, i.e., slightly tapered, through which a passageway 90 extends in communication with the surgical tubing 84. The port 10 has a surgical-type outlet tube 92 extending through the outlet 22 of the outlet arm 12 so as to be in communication with the outlet bore 20. A surgical type inlet tube 94 is similarly connected to the second inlet arm 16 so as to provide a source of fluid to the central chamber 32.

A valve 100 according to the present invention is shown disposed within the first inlet arm bore 24. The valve 100 is seen to consist of the cannula 34 and hub 40 shown in FIG. 3 disposed within the valve element 56 shown in FIG. 4. As will be seen in FIG. 5, the valve element first portion 58 at its base 60 is at least even with and should extend slightly beyond the inlet 26 of the inlet arm 14. By slightly extending beyond the inlet 26, rather than being recessed therein as is the case in the prior art, the base 60 can be readily swabbed with disinfectant prior to use to insure sterility during the utilization of the valve 100, as described with respect to FIG. 6.

Figure 6:
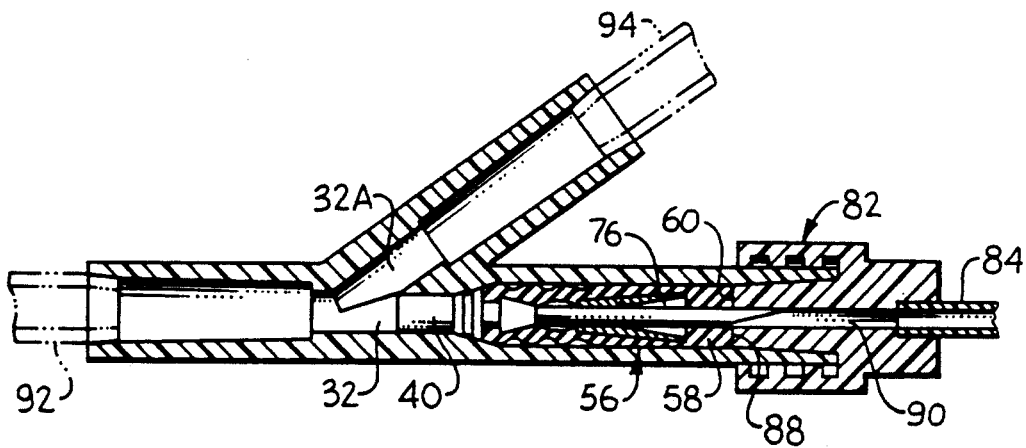
FIG. 6 is a cross-sectional view of the device of FIG. 5 with the female Luer fitting attached to open the valve.

Referring now to FIG. 6, the port 10 shown in FIG. 5 is shown with the Luer fitting 82 attached to the first inlet arm 14. In the attachment process, the Luer fitting nose 88 presses against the base 60 of the valve element first portion 58 so as to compress the valve element third portion 68 against the hub 40 and the interior surface of the first inlet arm bore 24 at the connecting passage 36. This compression of the valve element third portion 68 permits the Luer fitting nose 88 to force the valve element first portion 58 onto the point 44 of the cannula 34 and, after the point 44 pierces the first portion 58, the first portion 58 is forced inwardly along the cannula 34 so as to open a path for fluid communication from the surgical tubing 84 through the passageway 90 formed in the Luer fitting 82 and the cannula lumen 46.

Because the valve element 56 is formed of a flexible and resilient material, such as latex or some similar elastomeric material, removal of the Luer fitting 82 from the first inlet arm 12 decompresses the valve element third portion 68 so that the valve element first portion 58 moves outwardly away from the hub 40 to its original position as shown in FIG. 5. The first portion 58 is made of a self-sealing material, so that the movement of the first portion 58 off of the cannula 34 and beyond the cannula point 44 then seals, once more, the fluid passageway which existed through the cannula lumen 46 in the utilization shown in FIG. 6.

Figure 7:
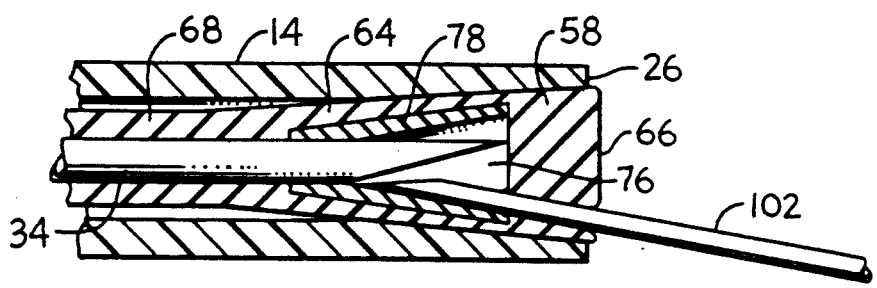
FIG. 7 is a cross-sectional view of the device shown in FIG. 5 illustrating its configuration in use for receiving an external cannula.

For certain requirements, such as an emergency procedure utilizing a hypodermic syringe with an attached cannula to rapidly inject a fluid into the central chamber 32, it may be inappropriate to attempt to use the Luer-type fitting 82. The valve of the present invention permits the alternate use of an external cannula to provide a fluid passage through the valve element first portion 58 to the cannula lumen 46. It is desirable to be able to insert such an external cannula within the cannula lumen 46. However, the valve of the present invention obviates such a necessity while, at the same time, assisting in such an alignment if desired. In this regard, referring now to FIG. 7, there is shown a partial sectional view of the inlet arm 14 and valve 56. In FIG. 7, an external cannula 102 which may be attached, for example, to a hypodermic syringe, is shown as having been inserted into the frustoconical passageway 76 formed within the valve element second portion 64. The frustonical sleeve 78 guides the external cannula 102 to a position adjacent the valve cannula 34. In an instance, such as is illustrated in FIG. 7, whether, because of the emergency nature of the procedure being performed or otherwise, the cannula 102 is not centered in the valve element first portion 58, the piercing of the valve element second portion inner surface 80 is avoided by the sleeve 78 guiding the cannula point 104 along its inner surface to the lumen 46 of the valve cannula 34. The contents of the syringe may then be expelled through the external cannula 102 into the second element passageway 76 even if the user fails to properly align the external cannula 102 with the valve cannula lumen 46 so as to be able to directly insert the external cannula 102 into the lumen 46. The user simply need insert the external cannula 102 until resistance is felt by reason of the external cannula 102 reaching the valve cannula 34 or the frustoconical sleeve 78, and then proceed to expel the contents of the hypodermic syringe, confident that the contents will pass through the valve cannula 34 into the central chamber 32 and then out the outlet arm 20 into the outlet tube 92.

Figure 8:
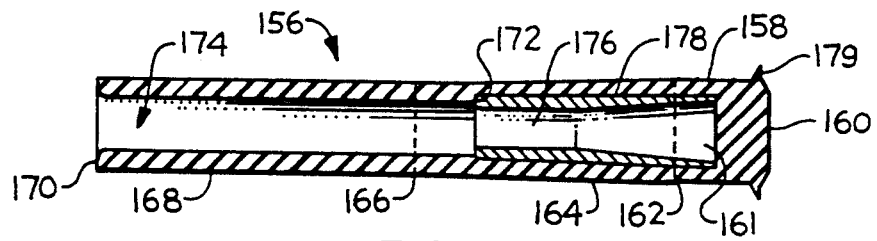
FIG. 8 is a cross-sectional view of a second embodiment of valve element for use in the medical valve of the present invention.

Referring now to FIG. 8, there is shown, as an alternate embodiment of a valve element for use in the present invention, a valve element 156. The valve element 156 has a first portion 158 which is of a generally cylindrical configuration in with a base 160 forming a first end of the valve element 156 and extending to a top 162 (shown in dotted lines). The valve element 156 has a second portion 164 which is generally frustoconical in exterior configuration over the majority of its length and tapers from the top 162, which forms the base of the second portion 164, to a second portion top 166, shown in dotted lines in FIG. 4. The valve element 156 has a third portion 168 which is generally cylindrical in configuration and extends from the second portion top 166 to a second end 170 of the valve element 156.

As will be seen in FIG. 8, the third portion 168 has an interior cylindrical passage 174 extending therethrough from the valve element second end 170 to the second portion top 166. The second portion 164 has an interior passage 176 which is generally frustoconical in configuration over most of its length so as to taper outwardly between a shoulder 172 formed adjacent the second portion top 166 and the first portion top 162. In the particular embodiment shown, the diameter of the passage of the third portion passage 174 is continued a short distance in the second portion passage 176 before opening onto the shoulder 172. The valve portions 158, 164, 168 are axially aligned with one another and provide a central passageway consisting of the passages 174 and 176 and a recess 161 formed in the interior of the first portion 158 adjacent the top 162, within which the hub 40 and cannula 34 are disposed, as shown in FIG. 9.

Seated within the cylindrical passage 176 against the shoulder 172 is a frustoconical sleeve 178 which is comparable to and performs the same functions as the sleeve 78. The valve element 156 has a peripheral sealing flap 179 formed on the first portion 158 adjacent the first end 160 to ensure closure at the conduit inlets as will be explained hereinafter.

Figure 9:
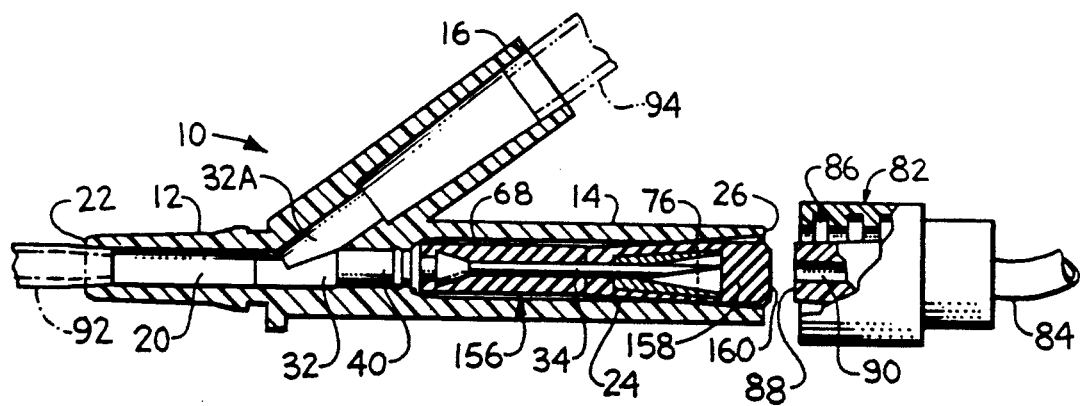
FIG. 9 is a cross-sectional view of the components of FIGS. 3 and 8 assembled in the body of FIG. 2 and ready to receive a medical device having a female luer fittings.

Referring now to FIG. 9, there is shown a side elevational view of the port 10 adapted for use with the valve element 156 in lieu of the valve element 56 shown in FIG. 5. Like reference numerals in FIG. 5 and 10 refer to like components. A valve element 156 according to the present invention is shown disposed within the first inlet arm bore 24. The valve element 156 encloses the cannula 34 and is fixed to the hub 40 in the same manner as the valve element 56 is fixed thereto in the embodiment of FIGS. 3-7. The sealing flap 179 closes the conduit 24 at the end 26 when the connector is not in use.

Figure 10:
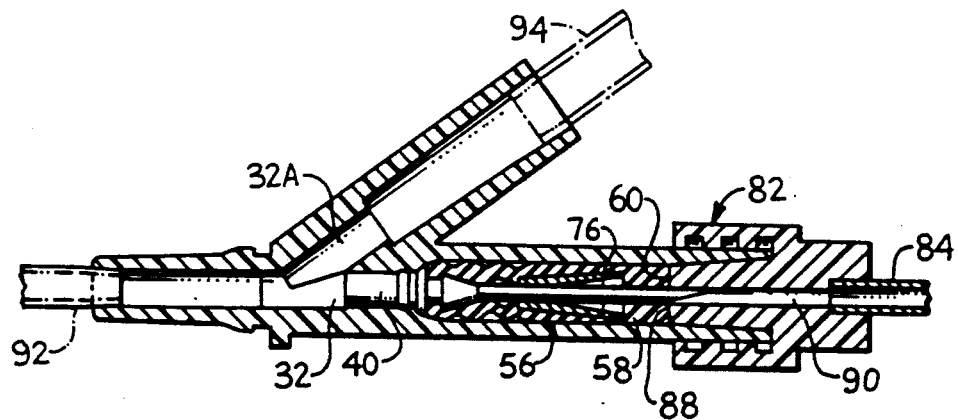
FIG. 10 is a cross-sectional view of the device of FIG. 9 with the female luer fitting attached to open the valve.

Referring now to FIG. 10, the port 10 shown in FIG. 9 is shown with the Luer fitting 82 attached to the first inlet arm 14. In the attachment process, the Luer fitting nose 88 presses against the base 160 of the valve element first portion 158 so as to compress the valve element third portion 168 against the hub 40 and the interior surface of the first inlet arm bore 24 at the connecting passage 36. This compression of the valve element third portion 168 permits the Luer fitting nose 88 to force the valve element first portion 158 onto the point 44 of the cannula 34 and, after the point 44 pierces the first portion 158, the first portion 158 is forced inwardly along the cannula 34 so as to open a path for fluid communication from the surgical tubing 84 through the passageway 90 formed in the Luer fitting 82 and the cannula lumen 46. The lack of rigidity of the first portion 158, when longitudinally compressed by attachment of the Luer fitting 82 may result in the first portion 158 collapse asymmetrically, resulting in the failure of the flap 179 to the conduit 24. To avoid such a failure, if required, tapered longitudinally extending fins 190 (only one of which is shown in FIG. 8) may be utilized to provide added frigidity against lateral deflection of the valve element first portion 158, if appropriate.

Because the valve element 156 is formed of a flexible and resilient material, such as latex or some similar elastomeric material, removal of the Luer fitting 82 from the first inlet arm 12 decompresses the valve element third portion 168 so that the valve element first portion 158 moves outwardly away from the hub 40 to its original position as shown in FIG. 9. The first portion 158 is made of a self-sealing material, so that the movement of the first portion 158 off of the cannula 34 and beyond the cannula point 44 then closes, once more, the fluid passageway which existed through the cannula lumen 46 when the medical connector of the present invention was being utilized as shown in FIG. 10.

The valve assemblies have been described heretofore in a particular embodiment specifically adapted for use in a Y-site port. However the valve assemblies of the present invention, and accompanying components, may be generally the medical field in connectors for various fluid used in the medical field in connectors for various fluid transfer applications.

Figure 12:
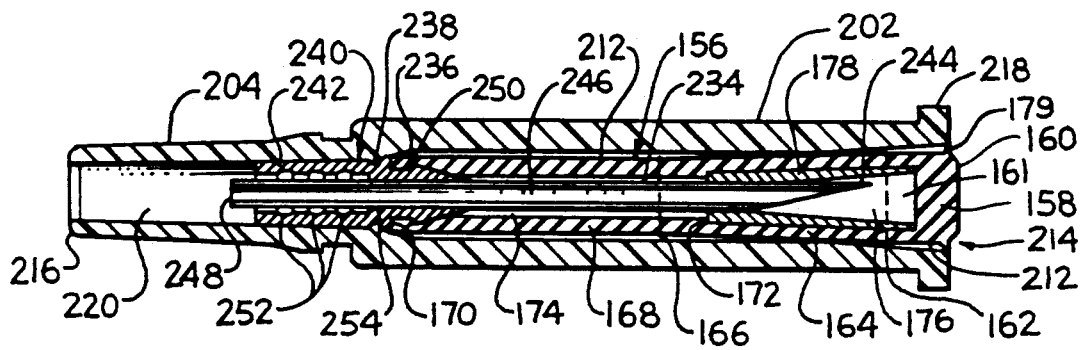
FIG. 12 is a view, in section, taken along lines 12—12 of FIG. 11.
Figure 11:
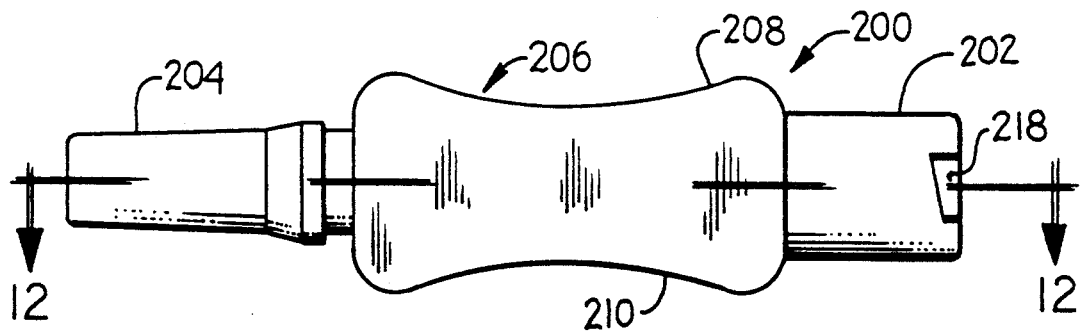
FIG. 11 is a plan view of a straight-through-type connector for use with the medical valve of the present invention, utilizing the valve element of FIG. 8.

Referring now to FIGS. 11 and 12, there is shown an alternate embodiment of a medical connector for use with the medical valve of the present invention. FIG. 11 is plan view of a straight-through-type medical connector 200 having an inlet portion 202 and an outlet portion 204. The connector 200 has a main body portion 206. Formed on the external surface thereof are two laterally-opposed gripping surfaces 208, 210 which assist the medical personnel during the use of the device, as will be apparent to those skilled in the art. As is seen in FIG. 12, a longitudinal passage 212 extends through the interior of the inlet portion 202. The inlet portion 202 has an inlet 214, from which the longitudinal passage 212 tapers inwardly slightly over most of its length, and a male-type Luer fitting 218. The outlet portion 204 has an outlet 216 onto which a longitudinal passage 220 opens. The main body portion 206 has a longitudinal passage 236 extending therethrough and opening into the inlet passage 212 and the outlet passage 220 so that all three passages 212, 220, 236 are axially aligned so as to provide a conduit through the connector 200. Disposed between the inlet 214 and the outlet 216 in the main body passage 236 is a hub 240 having a hollow hub body portion 242 which holds a cannula 234. An annular lip 238 is formed in the longitudinal passage 236 adjacent the outlet portion 204 and engages a complementary groove 254 formed in the hub body portion 242.

The hub body portion 242 has an annular locking recess 250 formed therein for engagement with the second end 170 of the valve element 156, so as to lock the valve element 156 to the hub 240. The cannula 234 has a point 244 which is disposed within the valve element in the same manner as that described heretofore with respect to FIG. 9. Opposite the point 244, the cannula 236 has an outlet 248 which opens into the outlet portion 204. The cannula outlet 248 extends beyond the hub body portion 242 so as to facilitate engagement of a fluid outlet tube (not shown). The hollow interior of the hub body portion 242 may have a series of annular recesses 252 formed therein to facilitate the gripping of the outlet tube by the connector when the outlet tube is slipped over the cannula outlet 248. The cannula 234 has a Lumen 246 extending therethrough between the point 244 and the cannula outlet 248 so as to provide a fluid passage through the conduit when the valve element first portion 160 is pressed onto and beyond the point 244 so as to pierce the first portion 160 in the same manner as was described heretofore with respect to the embodiments of FIGS. 1 through 10.

The valve element 156 shown in FIG. 12 is the same element as the valve element 156 heretofore described with respect to FIGS. 8 through 10, and like reference numbers in FIG. 12 refer to the same components as were described heretofore. Alternatively, the valve element 56 of the embodiment of FIGS. 1 through 7 may be utilized with the straight-through-type medical connector inlet portion 202 outlet portion 204 main body portion 206 hub 240 and cannula 234, if desired, although the valve element 156 of FIGS. 8 through 10 is presently preferred with respect to the embodiment of the present invention illustrated in Figs. 11 and 12.

The various components of the medical connector of the present invention are molded from conventional medical grade plastics. For example, valve elements 56 and 156 may be molded of medical grade latex, such as 7377-30 gum formulated to 80 Shore A durometer hardness, formulated and molded by West Company of Philadelphia, Pa. The port body 11 may be injection molded from medical grade polypropylene, such as grade PD-626 Pro-fax ® polypropylene distributed by Himont U.S.A., Inc. of Wilmington, Del. The sleeves 78 and 178 and cannula 34 may be made of #304 stainless steel. The needle hub 26 may be injection molded from medical grade polypropylene or from medical grade polycarbonate, such as from Calibre ®200-15 polycarbonate resin manufactured by Dow Chemical Company of Midland, Mich. The foregoing materials are described by way of example only, and are not intended to constitute limitations upon the practice of the present invention, as defined in the following claims.

The invention claimed is:

1. A medical valve for use in a conduit having an inlet portion and an outlet portion comprising:
    a hub;
    means for fixing said hub within the conduit so as to hold a hollow cannula having a pointed end disposed within the conduit so as to point toward the conduit inlet;
    an elongated flexible valve element having:
        a first portion which is generally circular in cross-section and which is solid at one end thereof so as to form a first end of the valve element;
        a second portion which is generally frustoconical in configuration over the majority of its length and has a longitudinal central passage extending therethrough which is axially aligned with the first portion; and
        a third portion which is generally circular in cross-section and has a longitudinal central passage extending therethrough which is axially aligned with the second portion central passage and extends from said second portion away from said first portion so as to terminate in a valve element second end opposite said valve element first end; and
    means for fixing the valve element within the conduit with respect to the hub so that the valve element is disposed in the conduit with the pointed end portion of the cannula contained within said central passages and so that the valve element first portion normally closes the conduit inlet portion.

2. A medical valve according to claim 1, and including a supplemental frustoconical sleeve disposed within the interior of the second valve portion passage so as to open outwardly away from the third valve portion toward the first valve portion.

3. A medical valve according to either claim 1 or claim 2, and in which the valve element is fixed with respect to the hub by the engagement of the valve element second end with the hub.

4. A medical valve according to claim 3, and in which the valve element first portion normally extends slightly beyond the inlet portion.

5. In a medical connector having a connector main body with an outlet and at least one inlet, and in which the inlet and the outlet each have a passage extending therefrom through the main body so as to be in communication with one another to provide a fluid passageway between the inlet and the outlet, the combination of:
    a hub fixed within the fluid passageway so as to hold a cannula within the main body so that the cannula is aligned to point away from the outlet;
    an elongated flexible valve element having:
        a first portion which is solid over at least a substantial portion of its length and is circular in cross-section,
        a second portion which is hollow and is generally frustoconical over at least the majority of its length and is axially aligned with said first portion so as extend away from said first portion; and
        a third portion which is hollow and circular in cross-section and is axially aligned with and connected to said second portion so as to extend away from said second portion to a valve element outlet formed thereon remote from said second portion;

and in which the third portion has a longitudinal passage extending axially therethrough and said second portion has a longitudinal passage extending axially therethrough so as to be in direct communication with and axially aligned with said third portion passage and to extend from said third portion passage to said first portion in axial alignment with said first portion;

a rigid frustoconical sleeve disposed within the second portion passageway so as to open outwardly from the third portion toward the first portion and enclose one end of the cannula; and means for attaching the valve element to the hub so that the valve element first portion normally closes the inlet.

6. A connector according to claim 5, and in which the means for attaching the valve element to the hub includes the valve element outlet.

7. A connector according to claim 6, and in which the valve element outlet engages an annular recess formed on the hub.

8. A connector according to any of claims 5, 6 or 7, and in which the first valve portion normally extends slightly beyond the inlet.

9. A connector according to claim 8, and including a second inlet attached to the connector body and having a passage therethrough which joins the fluid passageway downstream of the hub.

10. A medical valve according to claim 3, and in which the valve element first portion is generally frustoconical and solid along at least a major part of its length and tapers from a base formed at the first end of the element to a top;

the valve element second portion is axially aligned with the first portion so as to taper from a second portion base coincident with the first portion top to a second portion top; and the valve element third portion is generally cylindrical along at least a major part of its length and the valve element third portion longitudinal passage extends between the second end and the second portion, and in which said second portion longitudinal passage extends therethrough in direct communication with and is axially aligned with said third portion passageway, said second portion passageway being generally frustoconical over at least a substantial part of its length so as to open outwardly from the third portion toward the first portion and contain said cannula point.

11. A medical valve according to claim 10, and in which the valve element first portion normally extends slightly beyond the inlet portion.

12. A Y-site port medical connector of the type having a connector body with at least one inlet arm with an inlet passage terminating in an inlet and an outlet arm with an outlet passage terminating in an outlet, and in which the inlet arm passage is of generally circular cross-section over the majority of its length and extends from the inlet through the inlet arm so as to be in fluid communication with the outlet passage, and including:

a hub fixed within the inlet arm passage so as to hold a cannula within the inlet arm, the cannula thereby being axially aligned with the inlet arm, the cannula having a lumen which opens onto a point which points away from the outlet arm;

an elongated flexible valve element having:

a first portion which is generally circular in cross-section and which is solid at one end thereof so as to form a first end of the valve element;

a second portion which is generally frustoconical in configuration over the majority of its length and has a longitudinal central passage extending therethrough which is axially aligned with the first portion; and a third portion which is generally circular in cross-section and has a longitudinal central passage extending therethrough which is axially aligned with the second portion central passage and extends from said first portion so as to terminate in a valve element second end opposite said valve element first end; and means for fixing the valve element within the inlet arm with respect to the hub so that the valve element is disposed in the inlet passage with the pointed end portion of the cannula contained within said central passages and so that the valve element first portion normally closes the inlet passage at the inlet.

13. A connector according to claim 12, and including a supplemental frustoconical sleeve disposed within the interior of the second valve portion passage so as to open outwardly away from the third valve portion toward the first valve portion.

14. A connector according to either claim 12 or claim 13, and in which the valve element is fixed with respect to the hub by the engagement of the valve element second end with the hub.

15. A connector according to claim 14, and in which the valve element first portion normally extends slightly beyond the inlet portion.

16. A connector according to claim 14, and in which the valve element first portion is generally frustoconical and solid along at least a major part of its length and tapers from a base formed at the first end of the element to a top;

the valve element second portion is axially aligned with the first portion so as to taper from a second portion base coincident with the first portion top to a second portion top; and the valve element third portion is generally cylindrical along at least a major part of its length and the valve element third portion longitudinal passage extends between the second end and the second portion, and in which said second portion longitudinal passage extends therethrough in direct communication with and is axially aligned with said third portion passageway, said second portion passageway being generally frustoconical over at least a substantial part of its length so as to open outwardly from the third portion toward the first portion and contain said cannula point.

17. A connector according to claim 14, and including at least one additional inlet arm attached to the connector body and having an inlet passage which joins the outlet passage upstream of the outlet and downstream of the hub.

18. A connector according to claim 16, and including at least one additional inlet arm attached to the connector body and having an inlet passage which joins the outlet passage upstream of the outlet and downstream of the hub.

* * * * *